United States Patent
Koike et al.

(10) Patent No.: US 11,259,719 B2
(45) Date of Patent: Mar. 1, 2022

(54) VITAL SIGN INFORMATION RECORDING SYSTEM, VITAL SIGN INFORMATION ANALYZER, AND VITAL SIGN INFORMATION DISPLAY METHOD

(71) Applicant: NIHON KOHDEN CORPORATION, Tokyo (JP)

(72) Inventors: Teruhiro Koike, Tokorozawa (JP); Satoshi Saitoh, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 767 days.

(21) Appl. No.: 15/922,073

(22) Filed: Mar. 15, 2018

(65) Prior Publication Data

US 2018/0263571 A1 Sep. 20, 2018

(30) Foreign Application Priority Data

Mar. 15, 2017 (JP) .............................. JP2017-050359

(51) Int. Cl.
*A61B 5/11* (2006.01)
*A61B 5/00* (2006.01)
(Continued)

(52) U.S. Cl.
CPC .......... *A61B 5/1123* (2013.01); *A61B 5/0022* (2013.01); *A61B 5/02055* (2013.01);
(Continued)

(58) Field of Classification Search
CPC .... A61B 2560/0257; A61B 2562/0219; A61B 5/0006; A61B 5/0022; A61B 5/02055;
(Continued)

(56) References Cited

U.S. PATENT DOCUMENTS

2012/0289789 A1 11/2012 Jain et al.
2012/0289790 A1 11/2012 Jain et al.
(Continued)

FOREIGN PATENT DOCUMENTS

JP 2004-298444 A 10/2004
JP 2010-233953 A 10/2010
(Continued)

OTHER PUBLICATIONS

Japanese Office Action issued in Japanese Patent Application No. 2017-050359 dated Oct. 6, 2020.
(Continued)

*Primary Examiner* — Amanda K Hulbert
(74) *Attorney, Agent, or Firm* — Pearne & Gordon LLP

(57) ABSTRACT

A vital sign information recording system includes a data collector configured to collect behavior-associated information of a subject and vital sign information of the subject, and a display configured to display a presumed behavior of the subject and the vital sign information of the subject. At least one of the data collector and the display has a controller configured to determine the presumed behavior of the subject based on the behavior-associated information, and to display the presumed behavior of the subject and the vital sign information of the subject in a mutually associated manner on the display.

12 Claims, 13 Drawing Sheets

(51) Int. Cl.
*A61B 5/0205* (2006.01)
*G16H 40/67* (2018.01)
*G16H 20/30* (2018.01)
*G16H 50/30* (2018.01)
*A61B 5/1455* (2006.01)
*A61B 5/0245* (2006.01)

(52) U.S. Cl.
CPC .............. *G16H 20/30* (2018.01); *G16H 40/67* (2018.01); *G16H 50/30* (2018.01); *A61B 5/0006* (2013.01); *A61B 5/0245* (2013.01); *A61B 5/1455* (2013.01); *A61B 5/7275* (2013.01); *A61B 5/7285* (2013.01); *A61B 2560/0257* (2013.01); *A61B 2562/0219* (2013.01)

(58) Field of Classification Search
CPC ... A61B 5/0245; A61B 5/1123; A61B 5/1455; A61B 5/7275; A61B 5/7285; G16H 20/30; G16H 40/67; G16H 50/30
See application file for complete search history.

(56) References Cited

U.S. PATENT DOCUMENTS

| | | | |
|---|---|---|---|
| 2012/0289791 A1 | 11/2012 | Jain et al. | |
| 2016/0302680 A1* | 10/2016 | Narusawa | A61B 5/742 |
| 2016/0331247 A1 | 11/2016 | Albert | |
| 2019/0290208 A1* | 9/2019 | Toth | A61B 5/11 |

FOREIGN PATENT DOCUMENTS

| | | |
|---|---|---|
| JP | 2012-239891 A | 12/2012 |
| JP | 2013-246730 A | 12/2013 |
| JP | 2015-047253 A | 3/2015 |
| JP | 2016-202347 A | 12/2016 |
| JP | 2016-209020 A | 12/2016 |

OTHER PUBLICATIONS

Japanese Office action dated Mar. 30, 2021 issued in Japanese Patent Application No. 2017-050359.

* cited by examiner

FIG. 9

| PRESUMED BEHAVIOR | BODY MOTION | BODY POSITION | ATMOSPHERIC PRESSURE | TEMPERATURE |
|---|---|---|---|---|
| GETTING OUT OF BED | NO | STANDING | UNCHANGED | CHANGED |
| WALKING | LOW | STANDING | UNCHANGED | INCREASED |
| RUNNING | MIDDLE | STANDING | UNCHANGED | INCREASED |
| GOING UP STAIRS | LOW TO MIDDLE | STANDING | DECREASED | INCREASED |
| GOING DOWN STAIRS | LOW TO MIDDLE | STANDING | INCREASED | INCREASED |
| EATING | NO | STANDING (SITTING) | UNCHANGED | INCREASED |
| EXERCISING | HIGH | STANDING | UNCHANGED | INCREASED |
| BEFORE SHOWER/BATH | NO | STANDING (SITTING) | UNCHANGED | DECREASED |
| SHOWERING/ BATHING | NO | STANDING (SITTING) | INCREASED | INCREASED |
| SLEEPING | NO | NOT STANDING | UNCHANGED | UNCHANGED |
| ROLLING OVER IN BED | NO | STANDING | UNCHANGED | UNCHANGED |
| WALKING UPHILL | LOW | STANDING | DECREASED | INCREASED |
| RUNNING UPHILL | MIDDLE | STANDING | DECREASED | INCREASED |
| MOUNTAIN HIKING | YES | STANDING | FLUACTUATED | INCREASED |
| DIZZYING | NO | STANDING | INCREASED | UNCHANGED |
| FAINTING | YES | NOT STANDING | INCREASED | UNCHANGED |

FIG. 14

MODE 5

<BEHAVIOR SUMMARY>

| BEHAVIOR | TIME | MAXIMUM HR (BPM) | MINIMUM HR (BPM) | AVERAGE HR (BPM) | VENTRICULAR ARRHYTHMIA (NUMBER OF OCCURRENCE) | SUPRAVEN-TRICULAR ARRHYTHMIA (NUMBER OF OCCURRENCE) | CARDIAC ARREST (NUMBER OF OCCURRENCE) |
|---|---|---|---|---|---|---|---|
| GOING UP STAIRS | 13 MIN | 135 | 72 | 97 | 24 | 0 | 1 |
| WALKING | 2 HRS 12 MIN | 118 | 67 | 83 | 2 | 3 | 0 |
| RUNNING | 27 MIN | 147 | 118 | 126 | 35 | 8 | 0 |
| SHOWERING/ BATHING | 32 MIN | 121 | 93 | 107 | 8 | 5 | 2 |
| SLEEPING | 4 HRS 25 MIN | 68 | 57 | 62 | 0 | 0 | 0 |

<BEHAVIOR COMMENT>

ARRHYTHMIA FREQUENTLY OCCURRING DURING GOING UP STAIRS, RUNNING OR SHOWER/BATH. BE CAREFUL.
TEMPERATURE BEFORE SHOWER/BATH TOO LOW.
TEMPERATURE DURING SHOWER/BATH TOO HIGH.
WALKING EXERCISE RECCOMMENDED.
CLOSE TO TARGET HEART RATE (128 BPM) DURING WALKING EXERCISE.

VITAL SIGN INFORMATION RECORDING SYSTEM, VITAL SIGN INFORMATION ANALYZER, AND VITAL SIGN INFORMATION DISPLAY METHOD

CROSS-REFERENCE TO RELATED APPLICATION

The present application claims priority from Japanese Patent Application No. 2017-050359 filed on Mar. 15, 2017, the entire content of which is incorporated herein by reference.

BACKGROUND

The presently disclosed subject matter relates to a vital sign information recording system, a vital sign information analyzer, and a vital sign information display method.

In a test which is undertaken not under management of a medical personnel, such as an electrocardiographic test by the Holter method or a sleep apnea test, a subject himself/herself records what kinds of behaviors he/she performed during the test. The subject uses a physical tool, a function of an electronic device, or the like, to record the behaviors. For example, the subject records the behaviors by making a note on paper, or by operating subject's event keys of a test instrument.

The medical personnel checks both the record of the behaviors during the test, which was made by the subject himself/herself, and vital sign information recorded by a Holter monitor or a sleep apnea test instrument. When the record of the behaviors of the subject and the vital sign information of the subject are associated with each other, a highly accurate test result can be obtained. For example, based on the record of the behaviors such as exercising, going up/down stairs, getting out of bed, sleeping etc. reported by the subject, the medical personnel checks the vital sign information during each of the behaviors. Thus, the medical personnel can perform edition with high accuracy, and obtain a highly accurate test result.

To this end, the subject has to record the behaviors accurately in order to obtain a highly accurate test result. However, it is actually very troublesome for the subject to record the behaviors accurately. This becomes a burden on the subject. For this reason, there is a possibility that a recording omission or a recording mistake may arise.

A related art deals with a measurement of human behavior by selectively using various sensors such as an acceleration sensor, a barometer, a thermometer, and an electrocardiographic monitor (see, e.g., JP2012-239891A).

SUMMARY

One or more illustrative aspects of the presently disclosed subject matter provide a vital sign information recording system, a vital sign information analyzer, and a vital sign information display method, according to which a behavior of a subject and vital sign information of the subject can be displayed in a mutually associated manner.

According an aspect of the presently disclosed subject matter, the vital sign information recording system includes a data collector configured to collect behavior-associated information of a subject and vital sign information of the subject, and a display configured to display a presumed behavior of the subject and the vital sign information of the subject. At least one of the data collector and the display has a controller configured to determine the presumed behavior of the subject based on the behavior-associated information, and to display the presumed behavior of the subject and the vital sign information of the subject in a mutually associated manner on the display.

According another aspect of the presently disclosed subject matter, the vital sign information analyzer includes a behavior estimator configured to determine a presumed behavior of a subject based on behavior-associated information of the subject, and a display processor configured to display the presumed behavior of the subject and vital sign information of the subject in a mutually associated manner on a display.

According another aspect of the presently disclosed subject matter, the vital sign information display method includes receiving behavior-associated information of a subject and vital sign information of the subject, determining a presumed behavior of the subject based on the behavior-associated information, associating the presumed behavior of the subject and the vital sign information of the subject with each other, and displaying the behavior of the subject and the vital sign information of the subject in a mutually associated manner According another aspect of the presently disclosed subject matter, a non-transitory computer readable medium is provided. The non-transitory computer readable medium stores a program which, when executed by a computer, causes the computer to execute the method described above.

BRIEF DESCRIPTION OF DRAWINGS

FIG. 9 is a table illustrating a relationship between presumed behaviors and behavior-associated information;

FIG. 14 is a view illustrating a display mode 5 of the subroutine flow chart of FIG. 6.

DETAILED DESCRIPTION

Hereinafter, embodiments of the presently disclosed subject matter will be described in detail with reference to the drawings.

According to an embodiment of the presently disclosed subject matter, a data collector is configured to collect behavior-associated information and vital sign information, and a display is configured to determine a presumed behavior based on the behavior-associated information and to display the presumed behavior and the vital sign information in a mutually associated manner. Here, the behavior-associated information is information used for determining the presumed behavior of a subject.

Configuration of Vital Sign Information Recording System

Figure 1:
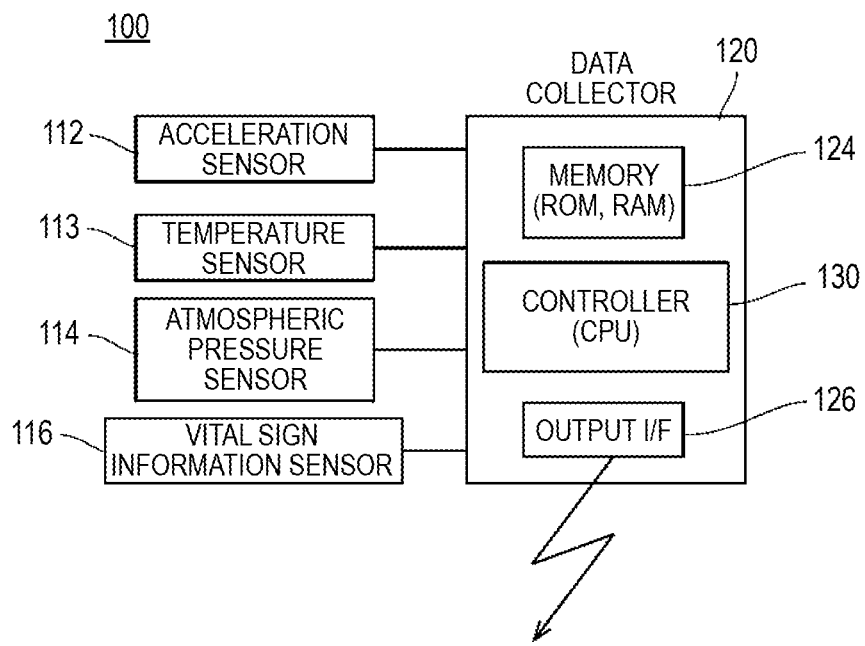
FIG. 1 is a block diagram illustrating a schematic configuration of a data collector of a vital sign information recording system.
Figure 2:
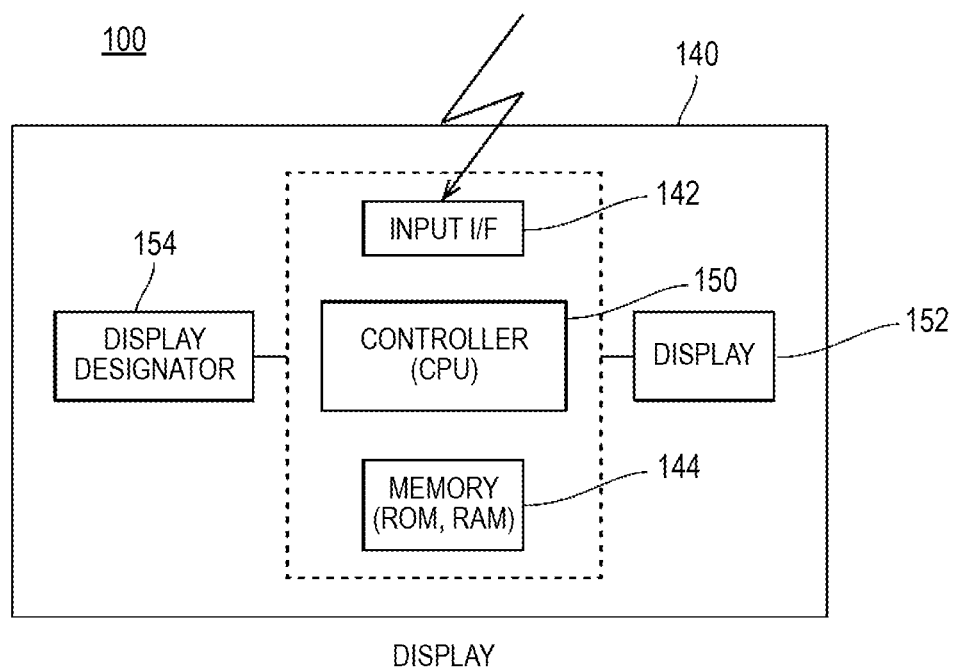
FIG. 2 is a block diagram illustrating a schematic configuration of a display of the vital sign information recording system.
Figure 3:
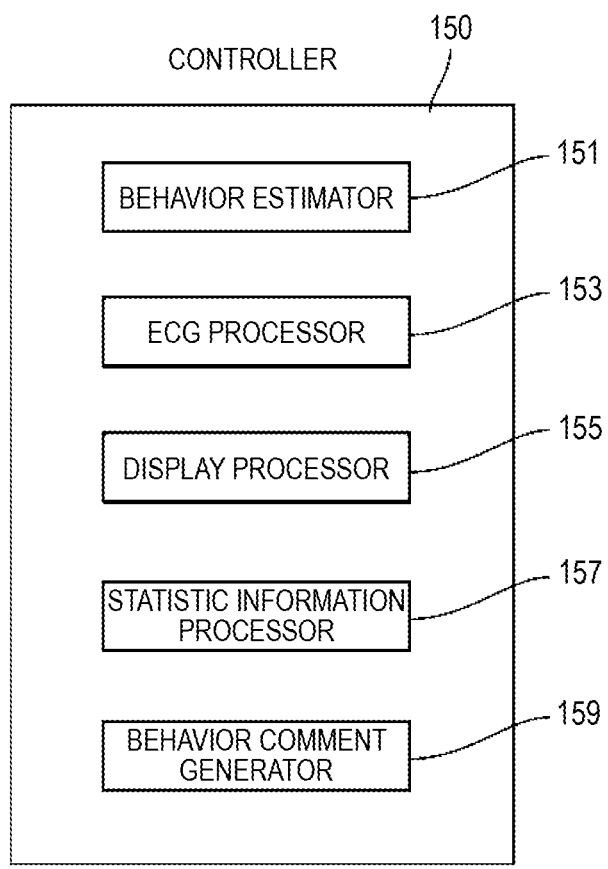
FIG. 3 is a block diagram of a controller provided in the data collector of FIG. 1 or in the display of FIG. 2.

FIG. 1 is a block diagram illustrating a schematic configuration of the data collector of the vital sign information recording system. FIG. 2 is a block diagram illustrating a schematic configuration of the display of the vital sign information recording system. FIG. 3 is a block diagram of a controller provided in the display of FIG. 2.

The vital sign information recording system 100 includes the data collector 120 of FIG. 1 and the display 140 of FIG. 2.

Configuration of Data Collector

The data collector 120 collects behavior-associated information for determining a presumed behavior of a subject, and vital sign information of the subject. To this end, the data collector 120 has a memory 124, a controller 130, and an output interface 126. An acceleration sensor 112, a temperature sensor 113 and an atmospheric pressure sensor 114, providing the behavior-associated information for the determination of the presumed behavior of the subject, are connected to the data collector 120. A vital sign information sensor 116 for acquiring the vital sign information of the subject is connected to the data collector 120.

The acceleration sensor 112, the temperature sensor 113 and the atmospheric pressure sensor 114 are attached to a body of the subject. The behavior-associated information detected by these sensors is used for determining the presumed behavior of the subject. The acceleration sensor 112 can measure a moving direction or a moving speed of the body of the subject. The temperature sensor 113 can measure a change in temperature around the subject. The atmospheric pressure sensor 114 can detect a gravity-direction position of the subject. In the illustrated example, the behavior-associated information is acquired by three sensors, i.e. the acceleration sensor 112, the temperature sensor 113 and the atmospheric pressure sensor 114. However, the behavior-associated information may be acquired from a group of sensors including not only these sensors but also or alternatively other sensors such as a humidity sensor. The presumed behavior of the subject can be determined by suitably combining information obtained from the group of sensors.

Various sensors such as the acceleration sensor 112, the temperature sensor 113 and the atmospheric pressure sensor 114, providing the behavior-associated information for the determination of a presumed behavior of the subject, and/or the vital sign information sensor 116 for acquiring the vital sign information of the subject may be provided in the data collector.

The vital sign information sensor 116 is a sensor for acquiring the vital sign information of the subject. When the vital sign information is ECG (electrocardiogram) information, the vital sign information sensor 116 is an ECG electrode attached to the body of the subject. Moreover, when the vital sign information is SpO2 information, the vital sign information sensor 116 is an SpO2 probe attached to a fingertip or an ear of the subject. Further, when the vital sign information is electroencephalogram (EEG) information, the vital sign information sensor 116 is an EEG electrode attached to a head of the subject. In addition, the vital sign information sensor 116 may be any of a sensor for detecting a respiration condition of the subject, a sensor for detecting pulses of the subject, a sensor for detecting blood pressure of the subject, a sensor for detecting myoelectricity of the subject, a sensor for detecting a body temperature of the subject, and a sensor for detecting an eyeball condition of the subject.

When the vital sign information sensor 116 is set as the ECG electrode, the data collector 120 can collect the ECG information as the vital sign information. In addition, when the vital sign information sensor 116 is set as the SpO2 probe, the data collector 120 can collect the SpO2 information as the vital sign information. Further, when the vital sign information sensor 116 is set as the EEG electrode, the data collector 120 can collect the EEG information as the vital sign information. In addition, when the vital sign information sensor 116 is set as the sensor which acquires vital sign information about the respiration, the pulses, the blood pressure, the myoelectricity, the body temperature, the eyeball, or the like, the data collector 120 can collect various information.

The memory 124 includes a read only memory (ROM) and a random access memory (RAM). The memory 124 stores the behavior-associated information acquired from the group of sensors including the acceleration sensor 112, the temperature sensor 113, the atmospheric pressure sensor 114 etc. into the RAM. The memory 124 also stores the vital sign information acquired from the vital sign information sensor 116 into the RAM. The memory 124 stores the acquired behavior-associated information and the acquired vital sign information in chronological order. When, for example, the data collector 120 is used as a Holter monitor, acceleration information, temperature information, atmospheric pressure information and ECG information for a period of about eight hours or longer are stored in the memory 124 in chronological order. A program for controlling operation of the controller 130 is stored into the ROM of the memory 124.

The output interface 126 transmits the behavior-associated information and the vital sign information stored in the memory 124, to the outside by wireless or by wire. When the output interface 126 is a type of transmitting the behavior-associated information and the vital sign information to the outside by wireless, the output interface 126 is provided with a transmitter. When the output interface 126 is a type of transmitting the behavior-associated information and the vital sign information to the outside by wire, the output interface 126 is provided with a connector.

The controller 130 includes a control processing unit (CPU) transmitting the behavior-associated information and the vital sign information stored in the memory 124, to the outside through the output interface 126.

Display

The display 140 displays a presumed behavior of the subject and the vital sign information of the subject. To this end, the display 140 has an input interface 142, a memory 144, a controller 150, a display portion 152, and a display designator 154.

The input interface 142 receives the behavior-associated information and the vital sign information of the subject sent from the output interface 126 of the data collector 120 (see FIG. 1) by wireless or by wire. When the input interface 142 is a type of receiving, as the inputs, the behavior-associated information and the vital sign information from the outside by wireless, the input interface 142 is provided with a receiver. When the input interface 142 is a type of receiving, as the inputs, the behavior-associated information and the vital sign information from the outside by wire, the input interface 142 is provided with a connector.

When the transmission between the output interface 126 and the input interface 142 is performed by wireless, user-friendliness is improved. On the other hand, when the transmission between the output interface 126 and the input interface 142 is performed by wire, the transmission is prevented from being easily affected by external noise. Accordingly, transmission reliability and transmission speed are improved.

The memory 144 is includes a read only memory (ROM), a random access memory (RAM) and a flash memory. The memory 144 stores the behavior-associated information and the vital sign information received as the inputs from the input interface 142, in the RAM or in the flash memory. A program for controlling operation of the controller 150 is stored in the ROM of the memory 144.

The controller 150 includes a control processing unit (CPU) which determines a presumed behavior of the subject based on the behavior-associated information stored in the memory 144, and displays the presumed behavior of the subject and the vital sign information of the subject in a mutually associated manner on the display portion 152. A detailed configuration of the controller 150 will be described later with reference to FIG. 3.

The display portion 152 is a liquid crystal display or an organic electroluminescence (EL) display which displays the presumed behavior of the subject determined by the controller 150, and the vital sign information of the subject in a mutually associated manner.

The display designator 154 designates a mode of displaying information on the display portion 152. Specifically, the display designator 154 instructs the controller 150 to display the information in one of the modes 1 to 5 illustrated in FIGS. 10 to 14.

A specific configuration of the controller 150 is illustrated in FIG. 3. The controller 150 has a behavior estimator 151, an ECG processor 153, a display processor 155, a statistic information processor 157, and a behavior comment generator 159.

Based the behavior-associated information stored in the memory 144, the behavior estimator 151 obtains at least a body motion of the subject, a change of a body position of the subject, an atmospheric pressure change and a temperature change, and determines a presumed behavior of the subject based on a combination of the body motion of the subject, the change of the body position of the subject, the atmospheric pressure change and the temperature change. The behavior estimator 151 determines the presumed behavior of the subject, based on changes in the body motion, the body position, the atmospheric pressure and the temperature. The presumed behavior of the subject can thus be determined from the behavior-associated information by the behavior estimator 151. A relationship between presumed behaviors to be determined by the behavior estimator 151 and the behavior-associated information are illustrated, for example, in FIG. 9.

The presumed behavior of the subject determined by the behavior estimator 151 is one of behaviors including getting out of bed, walking, running, going up stairs, going down stairs, eating, exercising, taking off clothes before shower/bath, showering/bathing, sleeping, rolling over in bed, walking uphill, running uphill, mountain hiking, dizzying, and fainting, as illustrated in FIG. 9. These presumed behaviors can be determined based on the behavior-associated information obtained from the group of sensors including the acceleration sensor 112, the temperature sensor 113, and the atmospheric pressure sensor 114. Since the presumed behavior of the subject is determined in detail, a highly accurate test result can be obtained.

From the vital sign information stored in the memory 144, the ECG processor 153 obtains an ECG, a heart rate, and an arrhythmia including at least tachycardia, bradycardia, ventricular arrhythmia, supraventricular arrhythmia, ST segment elevation, ST segment depression, cardiac arrest, irregular RR intervals, and atrial fibrillation. Since the ECG condition of the subject can be obtained in detail, a further accurate test result can be obtained by referring to the behavior of the subject.

The display processor 155 displays the behavior of the subject and the vital sign information in a mutually associated manner on the display portion 152. Accordingly, the medical personnel can view the behavior of the subject and the vital sign information in a mutually associated manner, and obtain a highly accurate test result.

The statistic information processor 157 calculates various statistic information for each kind of behavior of the subject based on the presumed behavior of the subject determined by the behavior estimator 151 and the vital sign information of the subject including the ECG, the heart rate and the arrhythmia obtained by the ECG processor 153. The calculated statistic information is stored in the memory 144. By the calculation of the statistic information, for example, it is possible to easily understand the association between the arrhythmia occurred and the subject's behavior.

Based on the presumed behavior of the subject determined by the behavior estimator 151 and the vital sign information of the subject including at least one of the ECG, the heart rate and the arrhythmia obtained by the ECG processor 153, the behavior comment generator 159 generates a behavior comment (see the behavior comments 400 of FIG. 14) for alerting the subject in connection with daily life. The medical personnel can refer to the behavior comment to give more meaningful advice to the subject.

The configurations of the vital sign information recording system 100, the data collector 120 and the display 140 have been described above. Next, operations of the vital sign information recording system 100, the data collector 120 and the display 140 will be described in detail with reference to FIGS. 4 to 6 and FIGS. 9 to 14.

Operation of Data Collector

Figure 4:
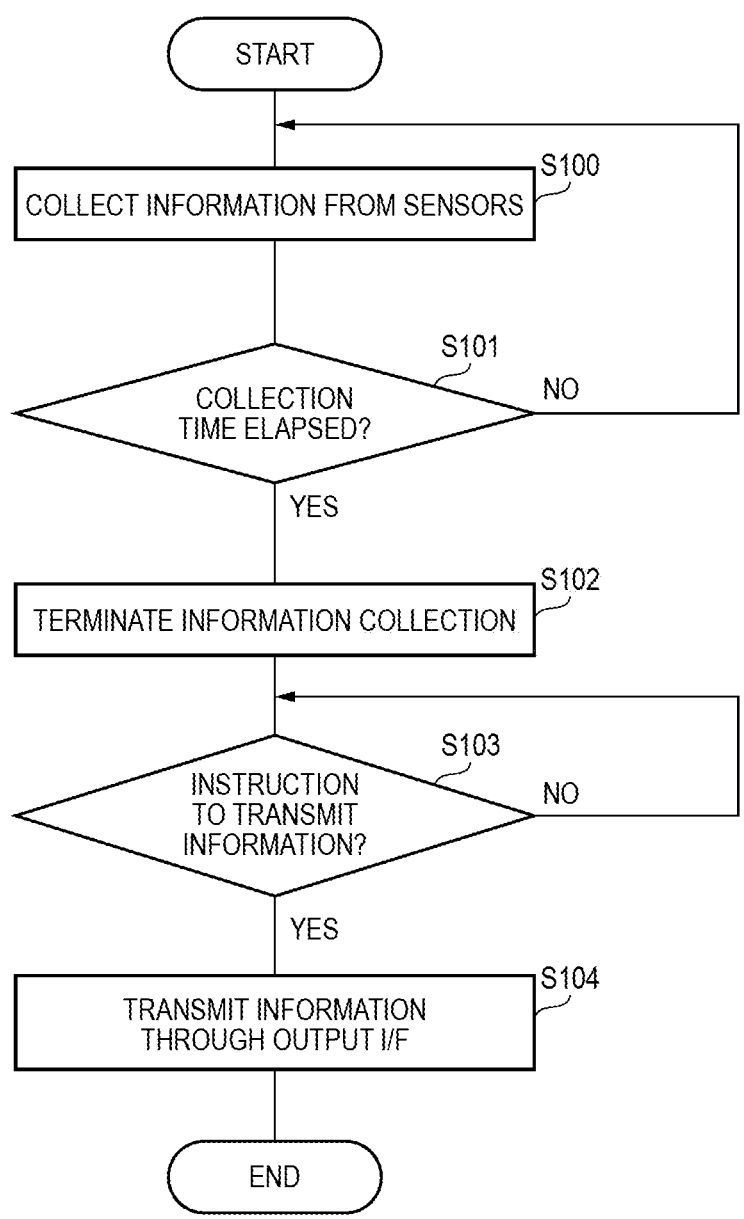
FIG. 4 is a flow chart of an operation of the data collector according to a first embodiment of the presently disclosed subject matter.

FIG. 4 is a flow chart of an operation of the data collector 120.

As illustrated in FIG. 1 the data collector 120 collects behavior-associated information including acceleration information from the acceleration sensor 112, temperature information from the temperature sensor 113, and atmospheric pressure information from the atmospheric pressure sensor 114. The data collector 120 also collects vital sign information from the vital sign information sensor 116 (S100). The behavior-associated information collected from the group of sensors including the acceleration sensor 112, the temperature sensor 113, the atmospheric pressure sensor 114, and the vital sign information collected from the vital sign information sensor 116 are stored in the memory 124 in chronological order.

A time is set for collecting the behavior-associated information and the vital sign information. For example, to collect a Holter ECG, the collection time is set at about 8 hours to 1 day. The data collector 120 determines whether the collection time has elapsed (S101). When the collection time has not elapsed (S101: NO), the data collector 120 returns to the step S100 to collect the behavior-associated information and the vital sign information. When the collection time has elapsed (S101: YES), the data collector 120 terminates the collection of the behavior-associated information and the vital sign information (S102).

The data collector 120 determines whether an instruction to transmit the behavior-associated information and the vital sign information is issued from the display 140 (S103). When the transmission instruction is not issued (S103: NO), the data collector 120 waits until the transmission instruction is issued. When there is a transmission instruction (S103: YES), the data collector 120 transmits the behavior-associated information and the vital sign information stored in the memory 124, in chronological order toward the display 140 through the output interface 126 (S104).

As such, the data collector 120 collects the behavior-associated information and the vital sign information, and transmits the behavior-associated information and the vital sign information toward the display 140.

Operation of Display

Figure 5:
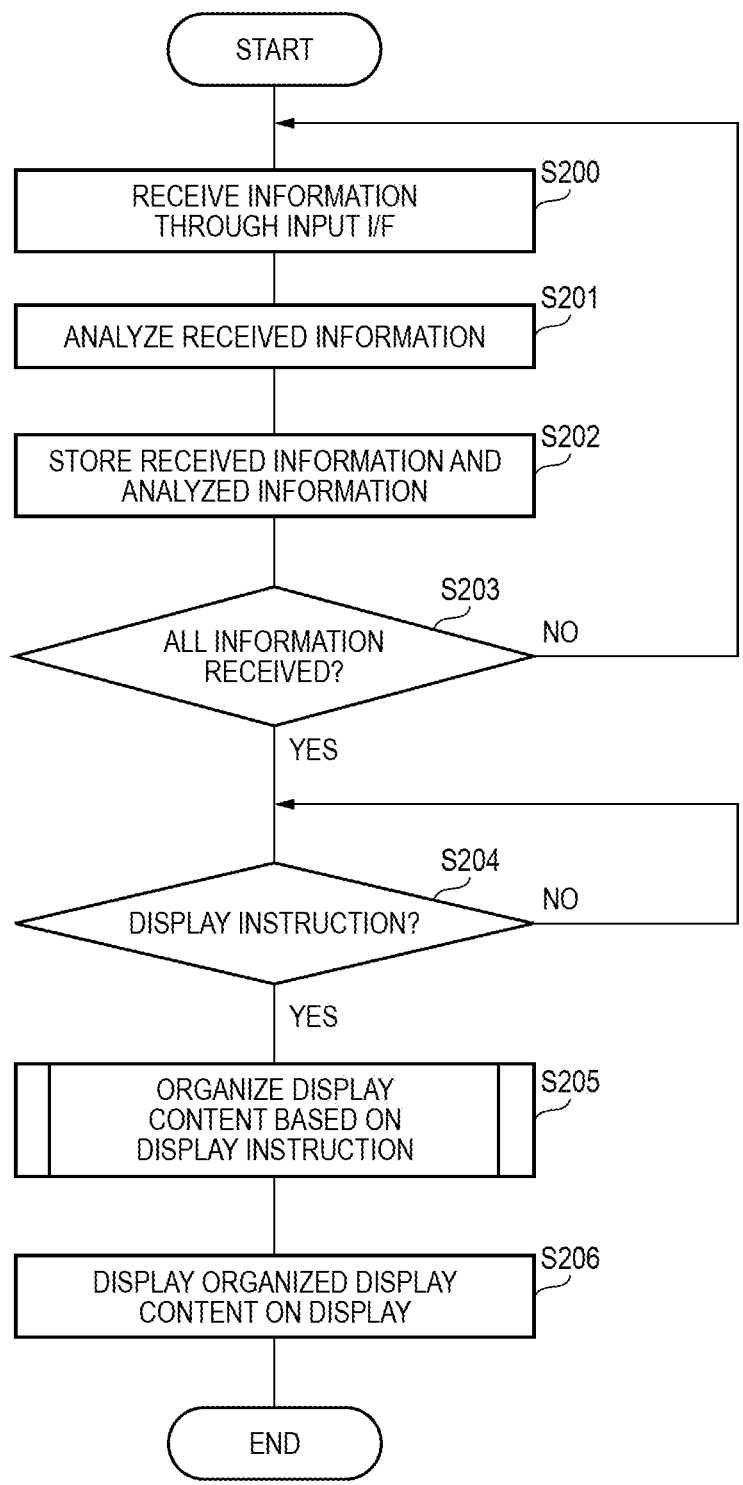
FIG. 5 is a flow chart of an operation of the display according to the first embodiment.

FIG. 5 is a flow chart of an operation of the display 140.

The display 140 receives the behavior-associated information and the vital sign information sent from the data collector 120, through the input interface 142 (S200).

The controller 150 analyzes the received behavior-associated information and the received vital sign information (S201). Specifically, from the received behavior-associated information, the behavior estimator 151 determines each of presumable behaviors of the subject such as getting out of bed, walking, running, going up stairs, going down stairs, eating, exercising, taking off clothes before shower/bath, showering/bathing, sleeping, rolling over in bed, walking uphill, running uphill, mountain hiking, dizzying, and fainting, as illustrated in FIG. 9. A relationship between combinations of the behavior-associated information detected respectively by the acceleration sensor 112, the temperature sensor 113 and the atmospheric pressure sensor 114 and the behaviors of the subject are stored in the memory 144.

For example, when it is determined that the subject has changed a body motion and taken a standing position based on the acceleration information detected by the acceleration sensor 112, that the atmospheric pressure has decreased stepwise based on the atmospheric pressure information detected by the atmospheric pressure sensor 114, and that the temperature has increased based on the temperature information detected by the temperature sensor 113, it is determined that the presumed behavior of the subject is "going up stairs". As such, the behavior estimator 151 analyzes the received behavior-associated information, and determines the presumed behavior of the subject.

From the received vital sign information, the ECG processor 153 obtains an ECG, a heart rate, and one of arrhythmias including at least tachycardia, bradycardia, ventricular arrhythmia, supraventricular arrhythmia, ST segment elevation, ST segment depression, cardiac arrest, irregular RR intervals, and atrial fibrillation. The ECG processor 153 determines the type of arrhythmia by analyzing the ECG.

The controller 150 stores the behavior-associated information and the vital sign information received through the input interface 142, the presumed behavior of the subject determined by the behavior estimator 151, and the ECG, the heart rate, and the arrhythmia type of the subject obtained by the ECG processor 153, into the memory 144 (S202).

The display 140 determines whether all the behavior-associated information and the vital sign information are received (S203). That is, the display 140 determines whether all the behavior-associated information and the vital sign information stored in the memory 124 of the data collector 120 are stored in the memory 144.

When all the behavior-associated information and the vital sign information are not received (S203: NO), the display 140 returns to the step S200 to repeat the steps S200 to S202 to store the behavior-associated information and the vital sign information into the memory 144, determine the presumed behavior of the subject and obtain the ECG, the heart rate and the arrhythmia until all the behavior-associated information and the vital sign information are received.

When all the behavior-associated information and the vital sign information are received (S203: YES), the display 140 determines whether there is a display instruction from the display designator 154 (S204). When there is no display instruction from the display designator 154 (S204: NO), the display 140 waits until a display instruction is issued. When there is a display instruction from the display designator 154 (S204: YES), the display processor 155 of the controller 150 organizes a content of display in accordance with the display instruction (S205). Details of how the display processor 155 organizes the display content in accordance with the display instruction will be described below with reference to the flow chart of FIG. 6.

The controller 150 displays the organized display content on the display portion 152 (S206).

Figure 6:
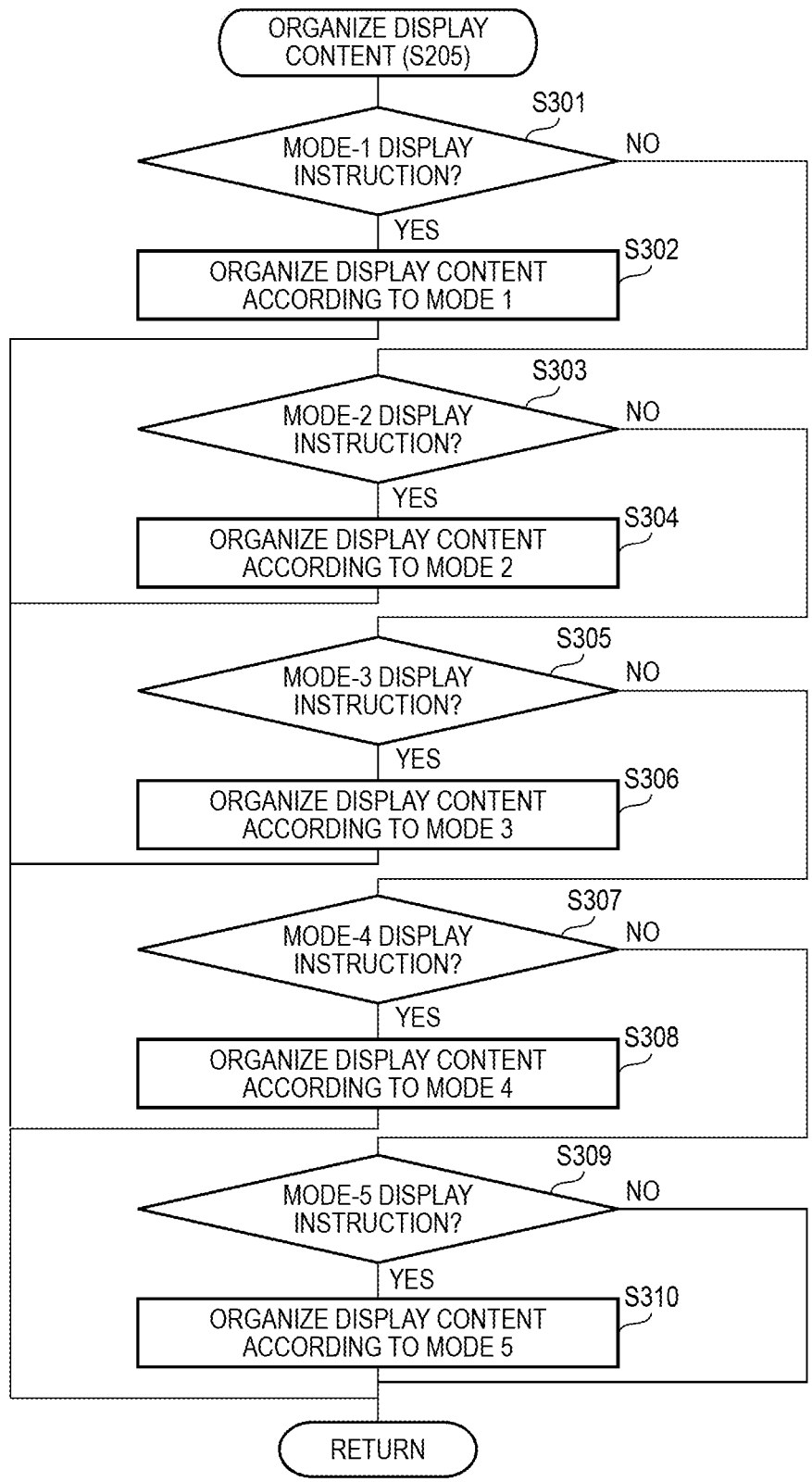
FIG. 6 is a subroutine flow chart of a step S205 of FIG. 5.
Figure 10:
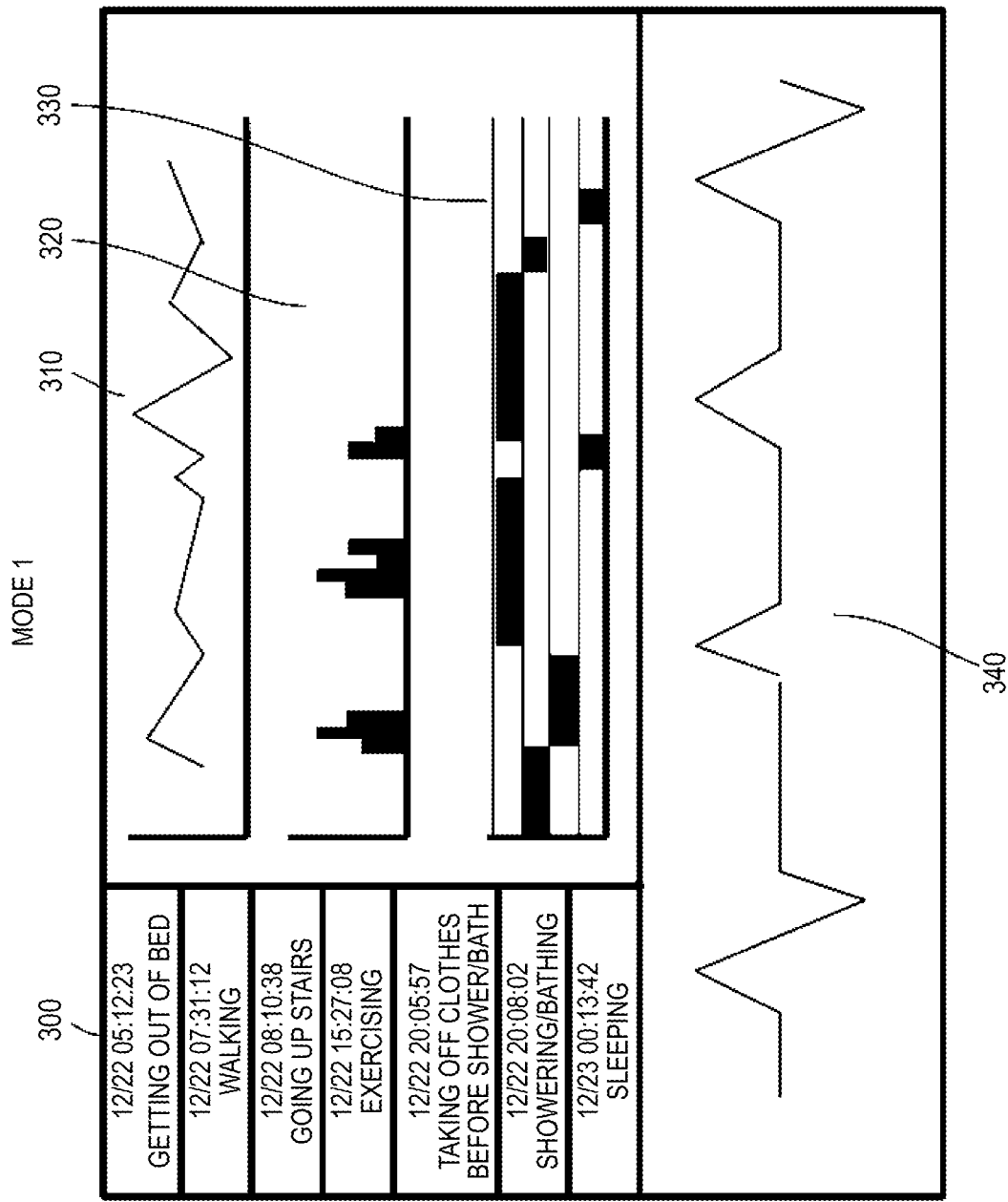
FIG. 10 is a view illustrating a display mode 1 of the subroutine flow chart of FIG. 6.

FIG. 6 is a subroutine flow chart of the step S205 of FIG. 5. FIGS. 10 to 14 are diagrams illustrating display modes 1 to 5 described in the subroutine flow chart of FIG. 6. The controller 150 determines whether a mode-1 display instruction is issued from the display designator 154 (S301). When there is a mode-1 display instruction (S301: YES), the controller 150 organizes a display content according to mode 1, as illustrated in FIG. 10 (S302).

Specifically, the display processor 155 (see FIG. 3) of the controller 150 lists presumed behaviors of the subject stored in the memory 144, from top to bottom in chronological order, and displays the presumed behaviors of the subject as a behavior list 300 on the display portion 152, as illustrated in FIG. 10. The behavior list 300 is generated based on the presumed behaviors of the subject determined by the behavior estimator 151. While the presumed behaviors are listed in chronological order in the illustrated embodiment, the presumed behaviors may be listed, for example, in accordance with categories of exercise-relevant events (going up/down stairs, walking, . . . , etc.), other daily behavior events (eating, showering/bathing, taking off clothes, sleeping, getting out of bed . . . etc.), symptoms (such as dizzying) etc.

The display processor 155 also displays a temporal variation of the heart rate stored in the memory 144, as a heart rate 310 covering a designated time (e.g. 8 hours, 1 hour, etc.) on a right side of the behavior list 300.

The display processor 155 also displays a temporal change of the body motion stored in the memory 144 as a body motion 320, from left to right in chronological order, on the right side of the behavior list 300 and below the heart rate 310. Each black segment illustrated in the body motion 320 designates a period of time when the subject had a body motion, and height of the black segment designates the intensity of the body motion corresponding to the height.

The display processor 155 also displays a temporal change of the body position stored in the memory 144 as a body position 330, from left to right in chronological order, on the right side of the behavior list 300 and below the body motion 320. From the place where each of bar segments illustrated in the body position 330 is located in an up-down direction, which body position the subject took, a supine position, a lateral decubitus position, a standing position or a prone position, can be known.

The display processor 155 also displays the ECG stored in the memory 144, as an ECG 340 covering a designated time (e.g. several tens of seconds etc.) on a lower side of the behavior list 300 and the body motion 320. For example, when any of the behaviors in the behavior list 300 is clicked, or when the inside of the graph of any of the heart rate 310, the body motion 320 and the body position 330 is clicked, an ECG waveform covering several tens of seconds centering around the clicked time point is displayed.

Thus, in mode 1, the behavior list 300, the heart rate 310, the body motion 320, the body position 330, and the ECG 340 are displayed on the display portion 152. Accordingly, a medical personnel can view the behaviors of the subject and the vital sign information of the subject in a mutually associated manner, and complement judgement of the medical personnel. Hence, the medical personnel can obtain a highly accurate test result.

Figure 11:
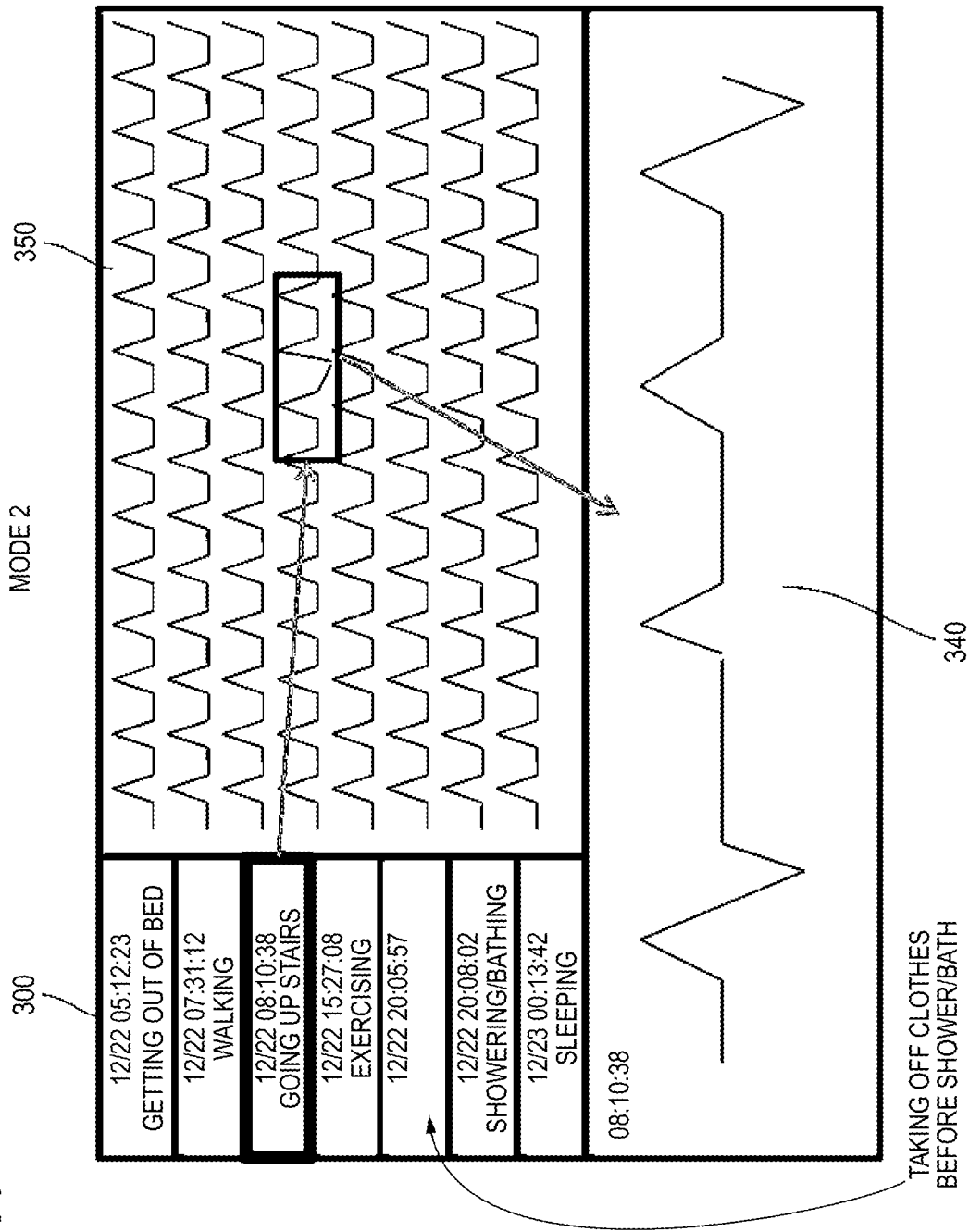
FIG. 11 is a view illustrating a display mode 2 of the subroutine flow chart of FIG. 6.

Next, when there is no mode-1 display instruction (S301: NO), the controller 150 determines whether a mode-2 display instruction is issued from the display designator 154 (S303). When there is a mode-2 display instruction (S303: YES), the controller 150 organizes a display content in accordance with mode 2 as illustrated in FIG. 11 (S304).

Specifically, the display processor 155 of the controller 150 lists presumed behaviors of the subject stored in the memory 144, from top to bottom in chronological order in a similar manner to or the same manner as in FIG. 10, and displays the presumed behaviors of the subject as a behavior list 300 on the display portion 152.

The display processor 155 also displays an ECG 350 stored in the memory 144, on a right side of the behavior list 300. The ECG 350 is compressed to some degree and used to check the state of the ECG waveform roughly or to check a long-term variation of the ECG waveform efficiently. Display time of the ECG waveform can be switched among, for example, 5 minutes, 10 minutes, 15 minutes, 30 minutes and 1 hour.

Further, in a similar manner to or the same manner as FIG. 10, the display processor 155 displays an ECG stored in the memory 144, as an ECG 340 covering a designated time on a lower side of the behavior list 300 and the ECG 350. The ECG 340 is an ECG displayed in an enlarged manner. The ECG 340 is enlarged so that the state of the ECG waveform can be checked in detail. For example, the ECG 340 is enlarged so that a P wave can be checked. In the ECG 340, a time including a time point at which a corresponding one of the behaviors in the behavior list 300 was clicked is displayed. A range between a start point and an end point of the display can be set desirably by a user.

In this manner, in mode 2, the behavior list 300, the ECG 350 with increased time width has been increased, and the ECG 340 with reduced time width are displayed on the display portion 152. Accordingly, for each presumed behavior of the subject, the medical personnel can search for an ECG waveform during the behavior, and easily check an arrhythmia caused by the behavior. Therefore, the medical personnel can view the behaviors of the subject and the vital sign information of the subject in a mutually associated manner, and complement judgement of the medical personnel. Accordingly, the medical personnel can obtain a highly accurate test result.

Figure 12:
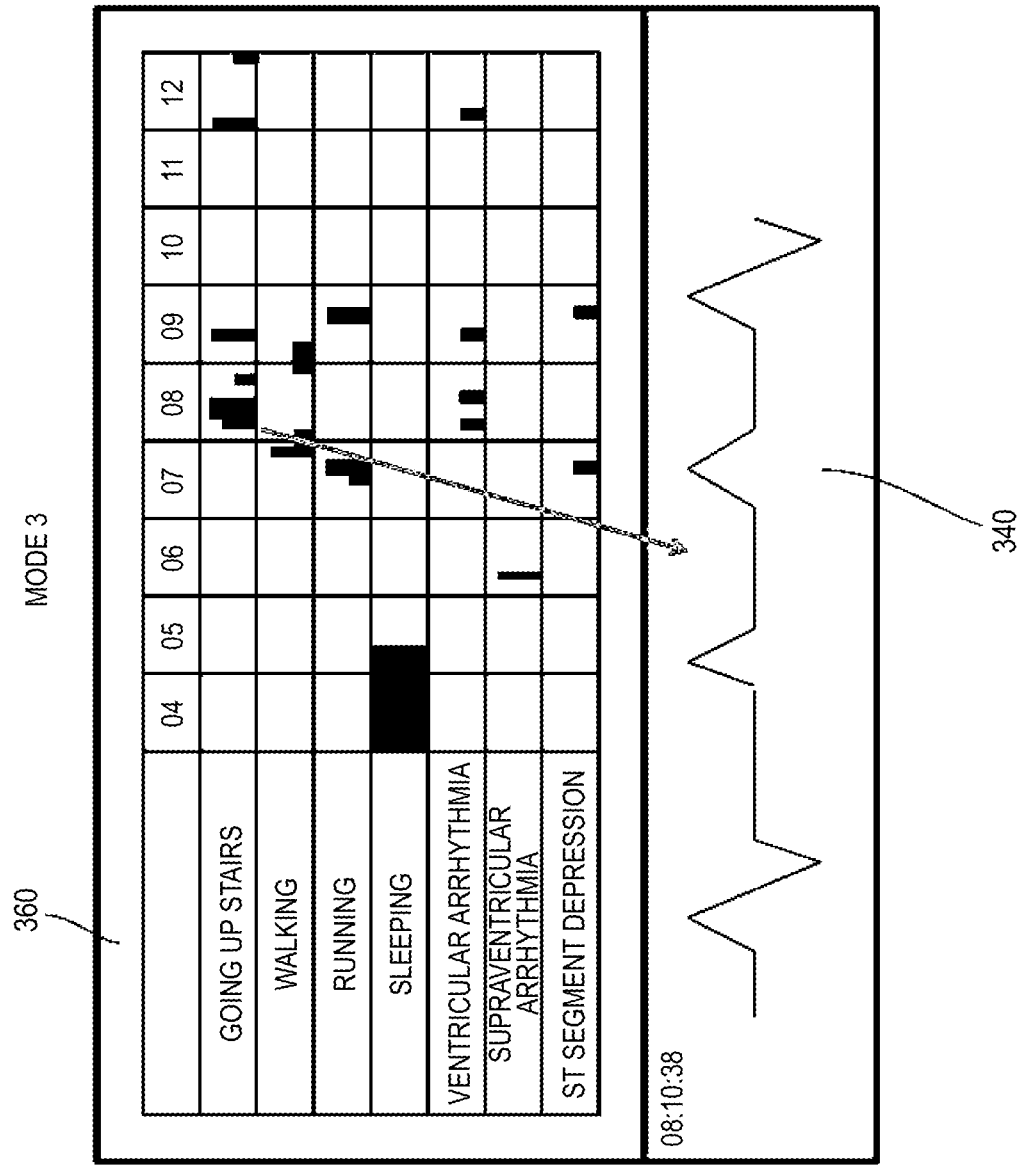
FIG. 12 is a view illustrating a display mode 3 of the subroutine flow chart of FIG. 6.

Next, when there is no mode-2 display instruction (S303: NO), the controller 150 determines whether a mode-3 display instruction is issued from the display designator 154 (S305). When there is a mode-3 display instruction (S305: YES), the controller 150 organizes a display content according to mode 3, as illustrated in FIG. 12 (S306).

Specifically, the display processor 155 of the controller 150 refers to the statistic information stored in the memory 144 to display a behavior-arrhythmia relationship diagram 360 on the display portion 152. In the behavior-arrhythmia relationship diagram 360, each presumed behavior of the subject and a time when the subject was performing the behavior are displayed by a bar graph. Accordingly, it is possible to check when and how often the subject performed the behavior during a test period in chronological order.

The behavior-arrhythmia relationship diagram 360 is displayed as follows. For example, when a graph is displayed by six bars per hour, each bar expresses ten minutes of a certain behavior. Each bar may be divided, for example, into ten graduations in a longitudinal direction. When a certain behavior lasts for longer than zero but shorter than one minute, one graduation of the bar is colored in black. When the behavior lasts for longer than five minutes but shorter than six minutes, six graduations of the bar are colored in black. When the presumed behavior is sleeping and the subject sleeps for the whole time section, i.e., 10 minutes, ten graduations of the bar are colored in black. That is, a period during which the subject is sleeping is colored in black.

Bar graphs representing ventricular arrhythmia, supraventricular arrhythmia, and ST segment depression in the behavior-arrhythmia relationship diagram 360 are displayed not by time but by the number of occurrences. For example, when one of the arrhythmias occurred more than zero but less than ten times in ten minutes, the bar for the arrhythmia is displayed by one graduation. When the arrhythmia occurred more than ten times but less than one hundred times in ten minutes, the bar for the arrhythmia is displayed by two graduations. When the arrhythmia occurred more than one hundred times but less than one thousand times, the bar for the arrhythmia is displayed by two graduations.

Further, in a similar manner to or the same manner as FIG. 10, the display processor 155 displays an ECG stored in the memory 144, as an ECG 340 covering a designated time on a lower side of the behavior-arrhythmia relationship diagram 360. For example, when a bar graph representing any of the behaviors in the behavior-arrhythmia relationship diagram 360 is clicked, an ECG waveform covering several tens of seconds centering around the clicked time point is displayed as the ECG 340.

In this manner, in mode 3, the behavior-arrhythmia relationship diagram 360 and the ECG 340 are displayed on the display portion 152. Accordingly, the medical personnel can easily check the presumed behaviors of the subject and frequencies of the arrhythmias in a mutually associated manner. Therefore, the medical personnel can obtain a highly accurate test result.

Figure 13:
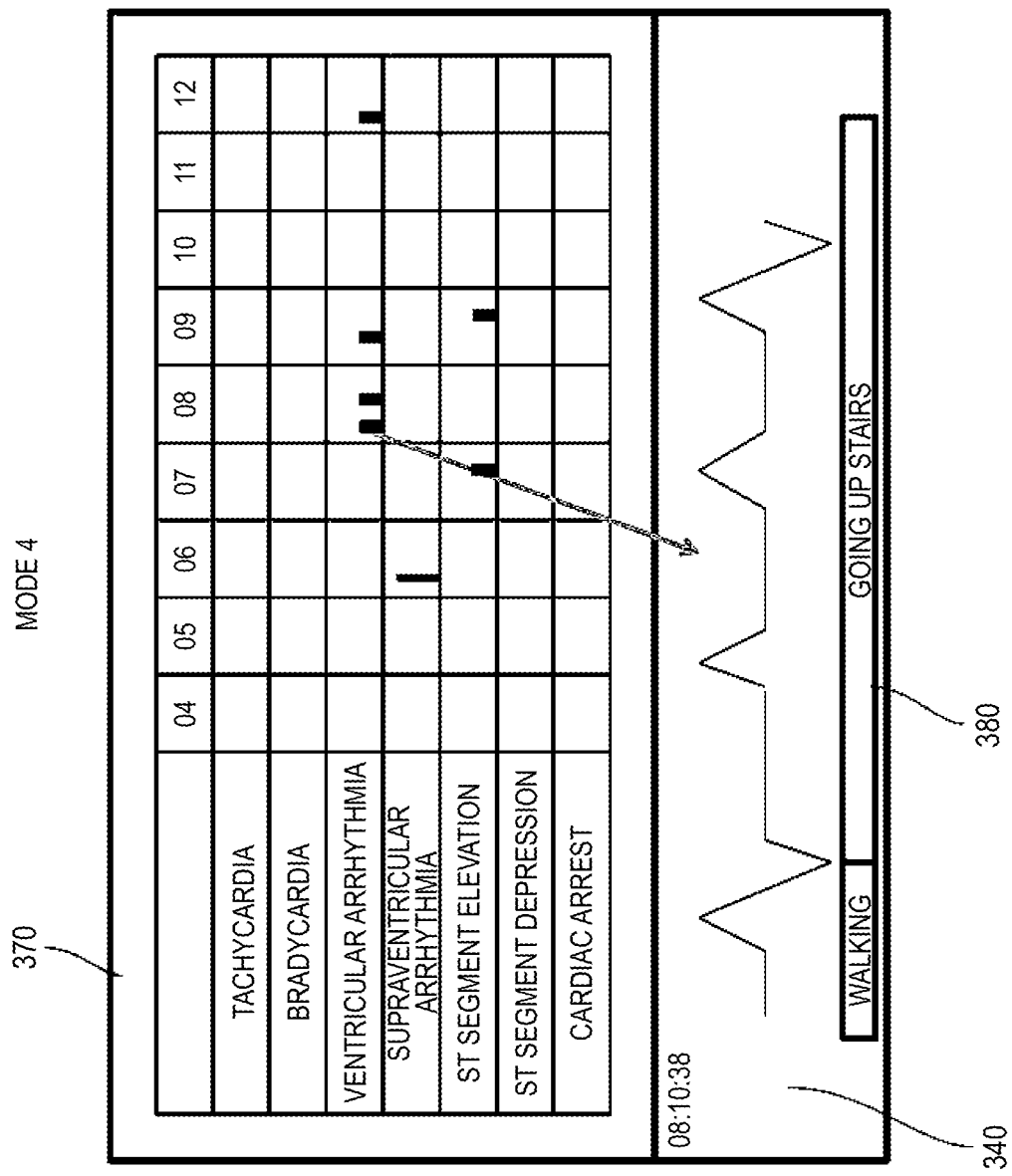
FIG. 13 is a view illustrating a display mode 4 of the subroutine flow chart of FIG. 6.

Next, when there is no mode-3 display instruction (S305: NO), the controller 150 determines whether a mode-4 display instruction is issued from the display designator 154 (S307). When there is a mode-4 display instruction (S307: YES), the controller 150 organizes a display content according to mode 4, as illustrated in FIG. 13 (S308).

Specifically, the display processor 155 of the controller 150 refers to the statistic information stored in the memory 144 to display an arrhythmia frequency chart 370 on the display portion 152. In the arrhythmia frequency chart 370, time points when arrhythmias occurred and frequencies of the arrhythmias are displayed in chronological order.

In addition, in a similar manner to or the same manner as FIG. 10, the display processor 155 displays an ECG stored in the memory 144, as an ECG 340 covering a designated time on a lower side of the arrhythmia frequency chart 370. For example, when ventricular arrhythmia which occurred at about 8 o'clock in the arrhythmia frequency chart 370 is clicked, an ECG waveform covering several tens of seconds centering around the clicked time point is displayed.

Further, the display processor 155 displays a behavior bar 380 corresponding to the ECG 340 under the ECG 340. The ECG 340 and the behavior bar 380 are displayed in parallel. Thus, it is possible to visibly judge during what kind of subject's behavior the arrhythmia occurred.

In this manner, the arrhythmia frequency chart 370, the ECG 340 and the behavior bar 380 are displayed in mode 4 on the display portion 152. Accordingly, the medical personnel can easily check the arrhythmia occurrence frequencies and the presumed behaviors of the subject in a mutually associated manner. Therefore, the medical personnel can obtain a highly accurate test result.

Next, when there is no mode-4 display instruction (S307: NO), the controller 150 determines whether a mode-5 display instruction is issued from the display designator 154 (S309). When there is a mode-5 display instruction (S309: YES), the controller 150 organizes a display content according to mode 5, as illustrated in FIG. 14 (S310).

Specifically, the display processor 155 of the controller 150 refers to the statistic information stored in the memory 144 to display a behavior summary 390 and a behavior comment 400 under the behavior summary 390 on the display portion 152.

The behavior summary 390 includes fields of behavior, time, maximum heart rate, minimum heart rate, average heart rate, the number of times of ventricular arrhythmia, the number of times of supraventricular arrhythmia, and the number of times of cardiac arrest.

When the medical personnel complementarily refers to the behavior summary 390, the medical personnel can easily recognize the heart beat state with respect to the behavior of the subject, the frequencies of occurrence of the arrhythmias, etc. Therefore, the medical personnel can obtain a more highly accurate test result. The behavior summary 390 is not limited to the illustrated items. The medical personnel may generate a behavior summary 390 including different items from the illustrated items as long as the medical personnel can obtain a more highly accurate test result from the behavior summary 390.

The behavior comments 400 are generated by the behavior comment generator 159 of the controller 150. The behavior comment generator 159 provides criteria for generating the behavior comments 400 such as "display a comment when the number of arrhythmias is not less than X during one of the behaviors of the subject", "determine a threshold of temperature before shower/bath in advance, and display a comment when the temperature is lower than the threshold", "determine a threshold of temperature during shower/bath in advance, and display a comment when the temperature is higher than the threshold", "determine a threshold of a ratio of a walking time to an entire time recorded by the apparatus in advance, and display a comment when the ratio of the walking time is lower than the threshold", "display a comment when the number of arrhythmias is not less than X in a high exercise intensity state (running etc.)", and "obtain an average heart rate of an ECG during a behavior time of walking, and display a comment when the heart rate of the subject is lower than the average heart rate".

When the statistic information stored in the memory 144 is referred to and the statistic information agrees with any of the criteria for generating the behavior comments 400, the behavior comment generator 159 displays a comment corresponding to the criterion on the display portion 152. The behavior comments 400 are optional, and are not limited to the illustrated examples. The medical personnel may generate a behavior comment 400 containing other items than the illustrated items as long as the behavior comment 400 is provided for making comments about a more highly accurate test result.

When the display in the display mode 5 is completed, the controller 150 terminates the process of the flow chart of FIG. 6 and moves to the step S206 of the flow chart of FIG. 5. When there is no mode-5 display instruction (S309: NO), the controller 150 also moves to the step S206 of the flow chart of FIG. 5.

In this manner, the behavior summary 390 and the behavior comment 400 are displayed in mode 5 on the display portion 152. Accordingly, the medical personnel can view the behavior summary 390 and the behavior comment 400 to obtain a highly accurate test result, and can provide comments about the test result.

According to another embodiment of the presently disclosed subject matter, a data collector 120 is configured to collect behavior-associated information and vital sign information, to determine a presumed behavior based on the collected behavior-associated information, and to analyze the vital sign information, and a display 140 is configured to display the presumed behavior and the analyzed vital sign information.

Configuration of Vital Sign Information Recording System

The vital sign information recording system 100 of this embodiment is different from the previously described embodiment in the configuration of a controller 130 of the data collector 120 and the configuration of a controller 150 of the display 140.

Configuration of Data Collector

The data collector 120 according to this embodiment is different from the data collector 120 according to the previous embodiment in that the behavior estimator 151 and the ECG processor 153 of the controller 150 illustrated in FIG. 3 are provided in the controller 130 of the data collector 120. The remaining configuration of the data collector 120 is the same as the data collector 120 of the previous embodiment. That is, the behavior-associated information and the vital sign information collected by the data collector 120 are analyzed by the data collector 120 itself.

Configuration of Display

The display 140 according to this embodiment is different from the display 140 of the previous embodiment in that only the display processor 155, the statistic information processor 157 and the behavior comment generator 159 of the controller 150 illustrated in FIG. 3 are provided in the controller 150 of the display 140. The remaining configuration of the display 140 is the same as that of the display 140 of the previous embodiment. That is, the display 140 makes display based on the behavior-associated information and the vital sign information analyzed by the data collector 120.

Next, operations of the data collector 120 and the display 140 according to the present embodiment will be described in detail with reference to flow charts of FIGS. 7 and 8.

Operation of Data Collector

Figure 7:
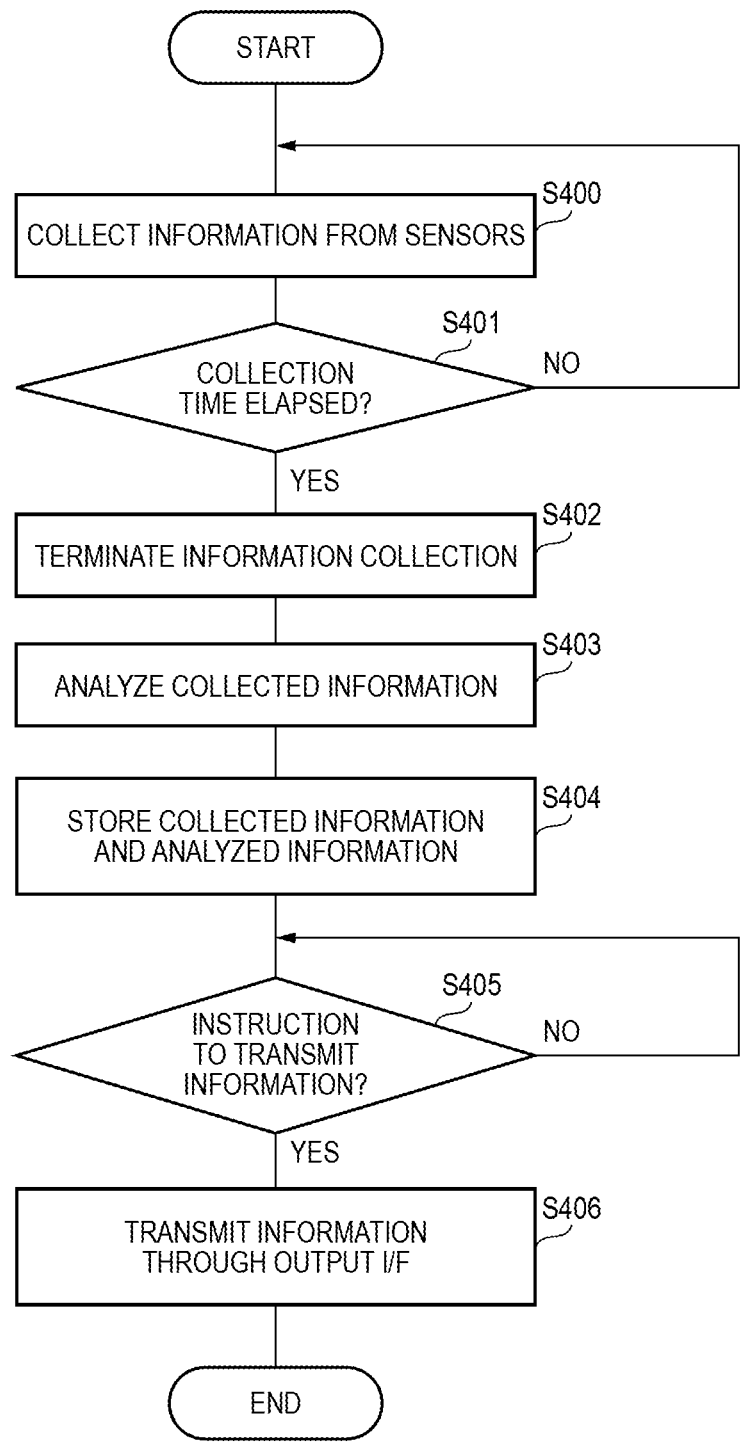
FIG. 7 is a flow chart of an operation of the data collector according to a second embodiment of the presently disclosed subject matter.

FIG. 7 is a flow chart of the operation of the data collector 120.

As illustrated in FIG. 1, the data collector 120 collects behavior-associated information including acceleration information from an acceleration sensor 112, temperature information from a temperature sensor 113, and atmospheric pressure information from an atmospheric pressure sensor 114. The data collector 120 also collects vital sign information from a vital sign information sensor 116 (S400). The behavior-associated information collected from the group of sensors including the acceleration sensor 112, the temperature sensor 113, the atmospheric pressure sensor 114, and the vital sign information collected from the vital sign information sensor 116 are stored in a memory 124 in chronological order.

A time is set for collecting the behavior-associated information and the vital sign information. The data collector 120 determines whether the collection time has elapsed (S401). When the collection time has not elapsed (S401: NO), the data collector 120 returns to the processing of S400 to collect the behavior-associated information and the vital sign information. On the other hand, when the collection time has elapsed (S401: YES), the data collector 120 terminates the collection of the behavior-associated information and the vital sign information (S402).

The controller 130 analyzes the received behavior-associated information and the received vital sign information (S403). Specifically, from the collected behavior-associated information, the behavior estimator 151 of the controller 130 determines a presumed behavior of a subject such as getting out of bed, walking, running, going up stairs, going down stairs, eating, exercising, taking off clothes before shower/bath, showering/bathing, sleeping, rolling over in bed, walking uphill, running uphill, mountain hiking, dizzying, and fainting, as illustrated in FIG. 9. A relationship between combinations of the information detected by the acceleration sensor 112, the temperature sensor 113 and the atmospheric pressure sensor 114 and the behaviors of the subject is stored in the memory 124.

From the collected vital sign information, the ECG processor 153 of the controller 130 obtains an ECG, a heart rate, and one of arrhythmias including at least tachycardia, bradycardia, ventricular arrhythmia, supraventricular arrhythmia, ST segment elevation, ST segment depression, cardiac arrest, irregular RR intervals, and atrial fibrillation. The ECG processor 153 of the controller 130 determines the type of the arrhythmia by analyzing the ECG.

The controller 130 stores the behavior-associated information and the vital sign information collected thus, the presumed behavior of the subject determined by the behavior estimator 151, and the ECG, the heart rate and the arrhythmia type of the subject obtained by the ECG processor 153, into the memory 124 (S404).

The data collector 120 determines whether an instruction to transmit the behavior-associated information and the vital sign information is issued from the display 140 (S405). When the transmission instruction is not issued (S405: NO), the data collector 120 waits until the transmission instruction is issued. On the other hand, when the transmission instruction is issued (S405: YES), the data collector 120 transmits the behavior-associated information and the vital sign information stored in the memory 124, the presumed behavior of the subject, and the ECG, the heart rate and the arrhythmia type of the subject toward the display 140 through an output interface 126 (S406).

As described above, the data collector 120 collects the behavior-associated information and the vital sign information to determine the presumed behavior based on the collected behavior-associated information and analyze the vital sign information. Then, the data collector 120 transmits the information about the presumed behavior and the analyzed vital sign information toward the display 140.

Operation of Display

Figure 8:
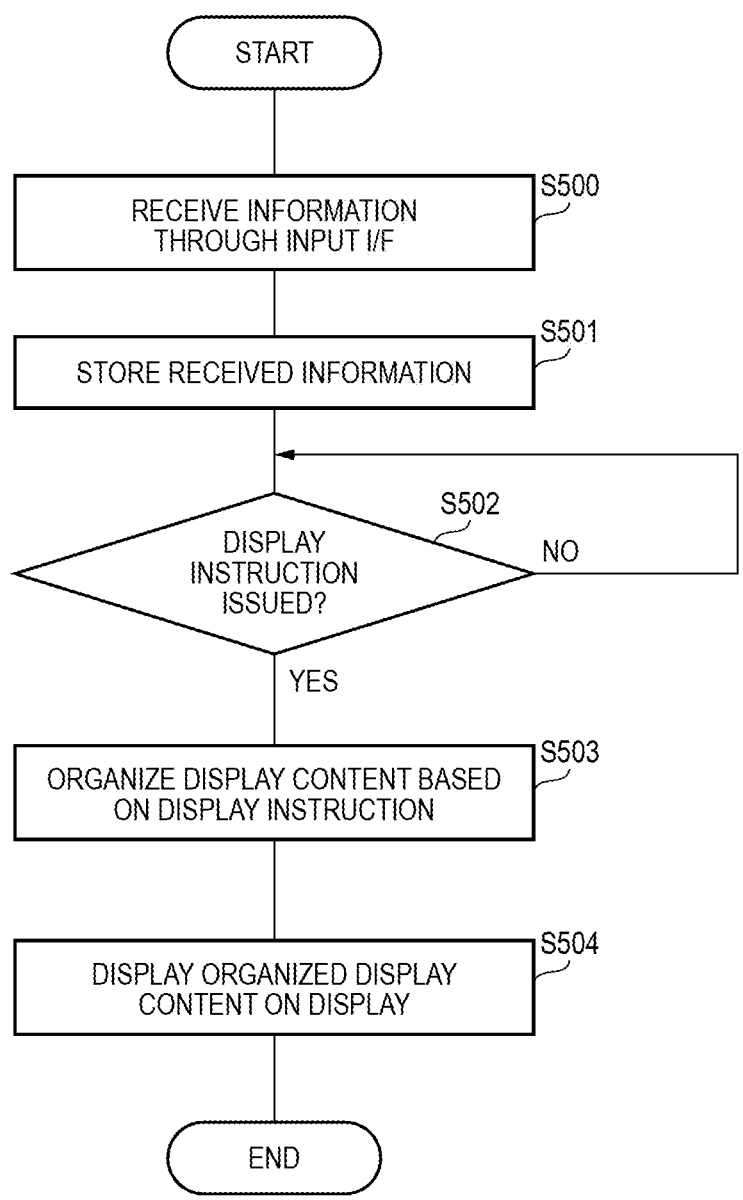
FIG. 8 is a flow chart of an operation of the display according to the second embodiment.

FIG. 8 is a flow chart of an operation of the display 140.

Through an input interface 142, the display 140 receives respective data or a set of data about the behavior-associated information with the vital sign information, the presumed behavior of the subject, and the ECG, the heart rate and the arrhythmia type of the subject, sent from the data collector 120 (S500).

The controller 150 stores the data received through the input interface 142 in a memory 144 (S501).

The controller 150 determines whether a display instruction is issued from a display designator 154 of the display 140 (S502).

When the display instruction is not issued from the display designator 154 (S502: NO), the controller 150 waits until the display instruction is issued. On the other hand, when the display instruction is issued from the display designator 154 (S502: YES), the display processor 155 of the controller 150 organizes a display content in accordance with the display instruction (S503). The organized display content corresponds to one of modes 1 to 5 illustrated in FIGS. 10 to 14.

The controller 150 displays the display content organized by the display processor 155 on the display portion 152 (S504).

According to the display 140 of the vital sign information recording system 100 according to this embodiment, the behavior of the subject and the vital sign information of the subject can be displayed in a mutually associated manner. Accordingly, a highly accurate test result can be obtained.

As described above, the overall configuration of the controller 150 in FIG. 3 may be provided in the controller 150 of the display 140 in the vital sign information recording system 100. On the other hand, a portion of the configuration of the controller 150 in FIG. 3 may be provided in the controller 130 of the data collector 120, and the remaining configuration of the controller 150 in FIG. 3 may be provided in the controller 150 of the display 140 in the vital sign information recording system 100. Thus, even in the case where the configuration of the controller 150 is divided into parts and the parts of the configuration of the controller 150 are provided in the data collector 120 and the display 140 separately, a medical personnel still can obtain a highly accurate test result. In addition, differently from Embodiments 1 and 2, the configuration of the controller 150 may be provided in each of the data collector and the display. With this configuration, the controllers 150 can be changed over from one to the other so that when, for example, the controller 150 of the display fails, the controller 150 of the display can perform processing according to the situation.

Vital Sign Information Analyzer

The display 140 of the first embodiment and the data collector 120 of the second embodiment are each configured as a vital sign information analyzer.

The vital sign information analyzer has the behavior estimator 151 configured to determine a presumed behavior of a subject based on behavior-associated information of the subject, and the display processor 155 configured to display the presumed behavior of the subject and vital sign information of the subject in a mutually associated manner on the display portion 152. The configurations and operations of the behavior estimator 151 and the display processor 155 are as described in connection with the first and second embodiments. With the vital sign information analyzer, the medical personnel can obtain a highly accurate test result.

Vital Sign Information Display Method

The invention also provides a vital sign information display method. The vital sign information display method is performed by the display 140. The procedure of the vital sign information display method is the same as the procedure of the operation flow chart illustrated in FIG. 5 or the procedures of the operation flow charts illustrated in FIGS. 7 and 8.

That is, according to the operation flow chart of FIG. 5, the vital sign information display method includes receiving behavior-associated information of a subject and vital sign information of the subject (S200), determining the presumed behavior of the subject based on the behavior-associated information and associating the presumed behavior of the subject and the vital sign information of the subject with each other (S201 to S203), and displaying the behavior of the subject and the vital sign information of the subject in a mutually associated manner (S204 to S206).

According to the operation flow charts of FIGS. 7 and 8, the vital sign information display method includes receiving behavior-associated information of a subject and vital sign information of the subject (S400 to S402), determining the presumed behavior of the subject based on the behavior-associated information (S403 and S404), associating the presumed behavior of the subject and the vital sign information of the subject with each other (S503), and displaying the behavior of the subject and the vital sign information of the subject in a mutually associated manner (S504).

According to the vital sign information display method described above, the behavior of the subject and the vital sign information of the subject can be displayed in a mutually associated manner. Thus, a highly accurate test result can be obtained.

Vital Sign Information Display Program

The vital sign information recording system 10 of the above embodiments has the configuration illustrated in FIGS. 1 and 2. The configuration of the vital sign information recording system 100 can be implemented by executing a program in a computer.

Here, the computer is an apparatus having at least one processor, and includes a vital sign information data collector having a processor. The program installed in the computer is a vital sign information display program which causes the computer to execute steps of receiving behavior-associated information of a subject and vital sign information of the subject, determining the presumed behavior of the subject based on the behavior-associated information, associating the presumed behavior of the subject and the vital sign information of the subject with each other, and displaying the behavior of the subject and the vital sign information of the subject in a mutually associated manner.

The vital sign information display program may be installed in the computer using a communication line via the Internet or through a data recording medium such as a magnetic disk, an optical disk, or a flash memory.

By installing the vital sign information display program in the computer, the computer functions as the vital sign information recording system 100.

By installing the vital sign information display program in the computer, the computer can display the behavior of the subject and the vital sign information of the subject in a mutually associated manner. Accordingly, the medical personnel can obtain a highly accurate test result.

What is claimed is:

1. A vital sign information recording system comprising:
   a data collector configured to collect behavior-associated information obtained from a plurality of body sensors attached to a subject and vital sign information obtained from at least one vital sign sensor attached to the subject, wherein the plurality of body sensors attached to the subject comprises an acceleration sensor, a temperature sensor and an atmospheric pressure sensor; and
   a display configured to display a presumed behavior of the subject based on the behavior-associated information, and the vital sign information of the subject,
   wherein the data collector comprises a first controller and the display comprises a second controller,
   wherein the second controller is configured to:
      determine the presumed behavior of the subject based on the behavior-associated information, and
      cause the display to display the presumed behavior of the subject and the vital sign information of the subject in a mutually associated manner on the display.

2. The vital sign information recording system according to claim 1, wherein the vital sign sensor attached to the subject is connected to the data collector, the vital sign information sensor including an ECG electrode, an SpO2 probe and an EEG electrode, and the data collector collects the vital sign information of the subject from the vital sign sensor.

3. The vital sign information recording system according to claim 2, wherein the vital sign information of the subject includes at least one in of ECG information acquired from the ECG electrode, SpO2 information acquired from the SpO2 probe, EEG information acquired from the EEG electrode, information acquired from a sensor detecting a respiration condition of the subject, information acquired from a sensor detecting pulses of the subject, information acquired from a sensor detecting blood pressure of the subject, information acquired from a sensor detecting myoelectricity of the subject, information acquired from a sensor detecting a body temperature of the subject, and information acquired from a sensor detecting an eyeball condition of the subject.

4. The vital sign information recording system according to claim 1, wherein the second controller comprises a behavior estimator configured to obtain at least a body motion of the subject, a body position of the subject, an atmospheric pressure change, and a temperature change, and to determine the presumed behavior of the subject based on a combination of the body motion, the body position, the atmospheric pressure change, and the temperature change.

5. The vital sign information recording system according to claim 4, wherein the presumed behavior of the subject determined by the behavior estimator includes at least one of going up stairs, going down stairs, eating, exercising, taking off clothes before shower or bath, showering or bathing, rolling over in bed, walking uphill, running uphill, mountain hiking, dizzying, and fainting.

6. The vital sign information recording system according to claim 4, wherein the second controller further comprises an ECG processor configured to obtain, from the vital sign information of the subject, an ECG, a heart rate, and an arrhythmia including at least one of tachycardia, bradycardia, ventricular arrhythmia, supraventricular arrhythmia, ST segment elevation, ST segment depression, cardiac arrest, irregular RR intervals, and atrial fibrillation.

7. The vital sign information recording system according to claim 4, wherein the second controller further comprises a display processor configured to display the behavior of the subject and the vital sign information of the subject in a mutually associated manner on the display.

8. The vital sign information recording system according to claim 6, wherein the first controller further comprises a statistic information processor configured to calculate statistic information for each kind of behaviors of the subject, based on the presumed behavior of the subject determined by the behavior estimator and the vital sign information of the subject including the ECG, the heart rate and the arrhythmia obtained by the ECG processor.

9. The vital sign information recording system according to claim 8, wherein the first controller further comprises a behavior comment generator configured to generate a behavior comment for alerting the subject in connection with daily life of the subject, based on the presumed behavior of the subject determined by the behavior estimator and the vital sign information of the subject including the ECG, the heart rate and the arrhythmia obtained by the ECG processor.

10. A vital sign information analyzer comprising:
a receiver configured to receive behavior-associated information obtained from a plurality of body sensors attached to a body of a subject and vital sign information obtained from at least one vital sign sensor attached to the subject, the plurality of body sensors comprising an acceleration sensor, a temperature sensor and an atmospheric pressure sensor;
a behavior estimator configured to determine a presumed behavior of a subject based on the behavior-associated information obtained from the plurality of body sensors attached to the subject;
a display processor configured to display the presumed behavior of the subject based on the behavior-associated information, and the vital sign information of the subject in a mutually associated manner on a display; and
a behavior comment generator configured to generate a behavior comment based on the presumed behavior of the subject and the vital sign information of the subject.

11. A vital sign information recording system comprising:
a plurality of body sensors attached to a body of a subject, the plurality of body sensors comprising an acceleration sensor, a temperature sensor and an atmospheric pressure sensor;
a data collector configured to collect behavior-associated information obtained from the plurality of body sensors attached to the subject and vital sign information obtained from a vital sign sensor attached to the subject;
a display configured to display a presumed behavior of the subject based on the behavior-associated information, and the vital sign information of the subject; and
an ECG processor configured to obtain, from the vital sign information of the subject, an ECG, and an arrhythmia including at least one of ventricular arrhythmia, supraventricular arrhythmia, ST segment elevation, ST segment depression, and cardiac arrest,
wherein at least one of the data collector and the display comprises a controller configured to determine the presumed behavior of the subject based on the behavior-associated information, and to display the presumed behavior of the subject and the vital sign information of the subject in a mutually associated manner on the display.

12. A vital sign information analyzer comprising:
a receiver configured to receive behavior-associated information obtained from a plurality of body sensors attached to a body of a subject and vital sign information obtained from at least one vital sign sensor attached to the subject, the plurality of body sensors comprising an acceleration sensor, a temperature sensor and an atmospheric pressure sensor;
a behavior estimator configured to determine a presumed behavior of a subject based on the behavior-associated information obtained from the plurality of body sensors attached to the subject;
a display processor configured to display the presumed behavior of the subject and the vital sign information of the subject in a mutually associated manner on a display; and
an ECG processor configured to obtain, from the vital sign information of the subject, an ECG, and an arrhythmia including at least one of ventricular arrhythmia, supraventricular arrhythmia, ST segment elevation, ST segment depression, and cardiac arrest.

* * * * *